US009911587B1

(12) United States Patent
Li et al.

(10) Patent No.: US 9,911,587 B1
(45) Date of Patent: Mar. 6, 2018

(54) METHODS AND SYSTEMS FOR QUANTITATIVE MASS ANALYSIS

(71) Applicant: Thermo Finnigan LLC, San Jose, CA (US)

(72) Inventors: Linfan Li, San Jose, CA (US); Derek J. Bailey, San Jose, CA (US)

(73) Assignee: Thermo Finnigan LLC, San Jose, CA (US)

(*) Notice: Subject to any disclaimer, the term of this patent is extended or adjusted under 35 U.S.C. 154(b) by 0 days.

(21) Appl. No.: 15/455,814

(22) Filed: Mar. 10, 2017

(51) Int. Cl.
*H01J 49/26* (2006.01)
*H01J 49/42* (2006.01)
*H01J 49/00* (2006.01)

(52) U.S. Cl.
CPC ........ *H01J 49/423* (2013.01); *H01J 49/0031* (2013.01); *H01J 49/0045* (2013.01)

(58) Field of Classification Search
CPC ... H01J 49/423; H01J 49/0045; H01J 49/0031
USPC ......................... 250/281, 282, 288, 290–293
See application file for complete search history.

(56) References Cited

U.S. PATENT DOCUMENTS 6,147,348 A 11/2000 Quarmby et al.
7,569,813 B2* 8/2009 Hager ................ H01J 49/0009 250/252.1
7,692,142 B2 4/2010 Schwartz et al.
8,258,462 B2 9/2012 Remes et al.
8,415,617 B2 4/2013 Schwartz
9,048,074 B2 6/2015 Senko
2005/0092910 A1* 5/2005 Geromanos .......... C12Q 1/6872 250/282
2011/0240844 A1* 10/2011 Ouyang .............. H01J 49/0404 250/282
2012/0223223 A1* 9/2012 Sugiyama ........... H01J 49/0031 250/282
2014/0364337 A1* 12/2014 Hermanson ............ G01N 33/60 506/12
2016/0181077 A1* 6/2016 Ouyang .............. H01J 49/0422 250/282
2016/0336163 A1 11/2016 Remes et al.

OTHER PUBLICATIONS

Schwartz et al., "A Two-Dimensional Quadrupole Ion Trap Mass Spectromter," J. Am. Soc. Mass. Spectrum., 13, 659-669, 2002.

* cited by examiner

*Primary Examiner* — Michael Maskell
(74) *Attorney, Agent, or Firm* — A. J. Gokcek

(57) ABSTRACT

A method of quantitative mass analysis of precursor species of different mass-to-charge (m/z) ratios from the same ion injection event is disclosed. A plurality of precursor ion species is introduced into a mass spectrometer at the same time, and isolated. A first subset of the isolated precursor ions having a first m/z ratio and a second subset of the isolated precursor ions having a second m/z ratio are fragmented. The fragmented ions are analyzed at the same time. A mass spectrum is generated for the fragment ions of the first and second subsets of precursor ions.

20 Claims, 7 Drawing Sheets

| Spiked Concentration (ug/ml) | 0.4 | 2 | 8 | 20 | 100 | 200 |
|---|---|---|---|---|---|---|
| RSD (%) QuanScan Rapid | 1.13 | 0.71 | 0.04 | 0.21 | 2.07 | 2.50 |

METHODS AND SYSTEMS FOR QUANTITATIVE MASS ANALYSIS

FIELD OF THE INVENTION

This invention relates to mass spectrometry based quantitative analysis. More specifically, this invention relates to quantitative mass analysis of product ions derived from multiple precursor species of different mass-to-charge (m/z) ratios injected into an ion trap mass analyzer in the same ion injection event.

BACKGROUND OF THE INVENTION

Conventional methods of quantitative mass analysis using ion trap mass spectrometers require the analyte and corresponding internal standard ions to be injected and analyzed from two time-separated ion injection events. Any fluctuations in the ionization process which occurs in between those two ion injection events introduces inaccuracies in the quantitative mass analysis for that particular measurement and subsequently leads to a bigger relative standard deviation (RSD) and uncertainty in such measurements.

What is needed is a quantitative mass analysis method that minimizes or eliminates errors introduced by the fluctuations in the ionization process and improves the uncertainty in the measurement.

SUMMARY

Embodiments of the present invention provide methods, systems, and apparatuses for quantitative mass analysis using ion trap mass analyzers (m/z analyzers). In one embodiment of the present invention, a method of operating an ion trap mass analyzer for quantification of analytes in a sample is provided. The analytes may comprise, in various implementations, therapeutic drugs or their metabolites, drugs of abuse or their metabolites, and endogenous substances such as creatinine. The method includes introducing sample ions into the ion trap mass analyzer. The sample ions, which are introduced into the ion trap in a single common or multiple common ion injection events, include analyte precursor ions having a first mass-to-charge ratio (m/z) or first m/z range and internal standard precursor ions having a second m/z or second m/z range. The method further includes concurrently m/z isolating both the analyte precursor ions and the internal standard precursor ions such that after the m/z isolation or isolations are effected only ions within the first precursor m/z range and the second precursor m/z range remain in the ion trap. The method also includes fragmenting (dissociating) the analyte precursor ions to generate analyte product ions, and fragmenting the internal standard precursor ions to generate internal standard product ions. The method also includes performing a mass analysis (m/z analysis) scan to mass-sequentially or mass-selectively eject the product ions to a detector to acquire a mass spectrum containing the analyte product ions and the internal standard product ions. The internal standard is selected such that both the internal standard and the analyte has at least one product ion species uniquely corresponding thereto; differently expressed, at least one characteristic product ion peak in the mass spectrum can be uniquely assigned to the analyte, and at least one other characteristic product ion peak in the spectrum can be uniquely assigned to the internal standard. The amount of the analyte in the sample may be determined using a calibration curve and intensities of the analyte unique product ions and the internal standard unique product ions in the mass spectrum. The product ions in the m/z spectrum are derived from precursor ions delivered to the ion trap in one or more common ion injection events.

The concurrently isolated analyte precursor ions and internal standard precursor ions may be fragmented (dissociated) successively or simultaneously to generate the analyte product ions and the corresponding internal standard product ions.

A notched or multi-notch waveform may be applied to concurrently isolate the analyte precursor ions and the internal standard precursor ions from any background ions.

The analyte and precursor ions may be fragmented using collision-induced dissociation (CID).

In another embodiment of the present invention, an ion trap mass spectrometer system is disclosed. The system includes an ion source configured to generate sample ions including analyte precursor ions having a first mass-to-charge ratio (m/z) and internal standard precursor ions having a second m/z. The system also includes an ion trap mass analyzer configured to receive the sample ions in a single ion injection event. The ion trap mass analyzer is provided with a controller programmed to apply voltages to the ion trap mass analyzer to cause the ion trap mass analyzer to perform the steps of concurrently isolating the analyte precursor ions and the internal standard precursor ions; fragmenting the analyte precursor ions to generate analyte product ions and fragmenting the internal standard precursor ions to generate internal standard product ions, wherein at least one characteristic product ion species of the analyte product ions uniquely corresponds to the analyte, and at least one characteristic product ion species of the internal standard product ions uniquely corresponds to the internal standard; and mass-sequentially or mass-selectively ejecting the ions to a detector to acquire a mass spectrum containing the analyte product ions and the internal standard product ions. The system is further provided with a data and control system programmed to determine the amount of the analyte in the sample using a relationship between intensities of the at least one characteristic analyte product ion species and at least one characteristic internal standard product ion species in the mass spectrum.

BRIEF DESCRIPTION OF THE DRAWINGS

FIG. 4A shows a conceptual depiction of a population of ionized multiple potential precursor species of different m/z ratios confined in the ion trap subsequent to a common ion injection event.

FIG. 4B shows, after the analyte and internal standard ions are isolated from any background ions, the analyte precursor ions are fragmented.

FIG. 4C shows the internal standard ions are fragmented, and the fragment ions of the analyte and the internal standard are analyzed by scanning at the same time. A mass spectrum is generated for the product ions of the analyte and the internal standard as shown.

DETAILED DESCRIPTION OF EMBODIMENTS

Figure 1:
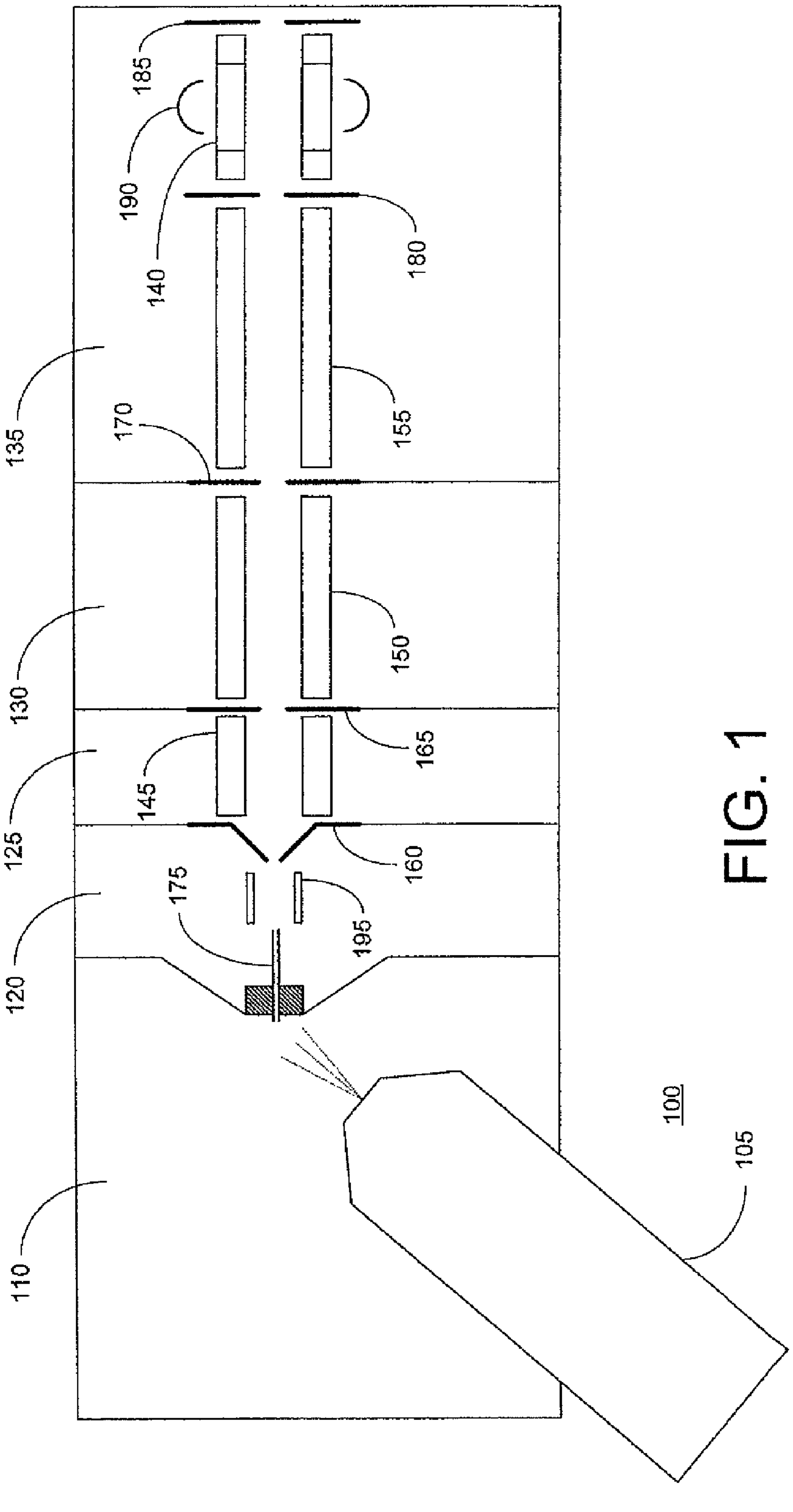
FIG. 1 is a schematic diagram of an ion trap mass spectrometer which may be operated in accordance with methods and systems embodying the present invention.

FIG. 1 illustrates an example of an ion trap mass spectrometer 100 which may be operated in accordance with embodiments of the present invention. It will be understood that certain features and configurations of mass spectrometer 100 are presented by way of illustrative examples, and should not be construed as limiting the methods of the present invention to implementation in a specific environment. An ion source, which may take the form of a conventional electrospray ion source 105, generates ions from a sample material. In other implementations, the ion source may take the form of a direct sampling ion source such as the Paper Spray ionization system available from Prosolia (Indianapolis, Ind.), in which a sample (e.g., a biological fluid such as blood or plasma) is deposited on a porous wicking material (e.g., paper) and electrosprayed from a tip of the material.

The ions are transported from ion source chamber 110, which for an electrospray source will typically be held at or near atmospheric pressure, through several intermediate vacuum chambers 120, 125 and 130 of successively lower pressure, to a vacuum chamber 135 in which ion trap 140 resides. Efficient transport of ions from ion source 105 to ion trap 140 is facilitated by a number of ion optic components, including quadrupole RF ion guides 145 and 150, octopole RF ion guide 155, skimmer 160, tube lens 195, and electrostatic lenses 165 and 170. Ions may be transported between ion source chamber 110 and first intermediate chamber 120 through an ion transfer tube 175 that is heated to evaporate residual solvent and break up solvent-analyte clusters. Intermediate chambers 120, 125 and 130 and vacuum chamber 135 are evacuated by a suitable arrangement of pumps to maintain the pressures therein at the desired values. In one example, intermediate chamber 120 communicates with a port of a mechanical pump (not depicted), and intermediate pressure chambers 125 and 130 and vacuum chamber 135 communicate with corresponding ports of a multistage, multiport turbo-molecular pump (also not depicted). Ion trap 140 includes axial trapping electrodes 180 and 185 (which may take the form of conventional plate lenses) positioned axially outward from the ion trap electrodes to assist in the generation of a potential well for axial confinement of ions, and also to effect controlled gating of ions into the interior volume of ion trap 140 in order to regulate the filling (injection) time of ion trap 140; for example, DC offset voltages applied to axial trapping electrode 180 (and/or electrodes located upstream in the ion path relative to axial trapping electrode 180) may be set to selectively allow or block the flow of ions into ion trap 140. A damping/collision gas inlet (not depicted), coupled to a source of an inert gas such as helium or argon, will typically be provided to controllably add a damping/collision gas to the interior of ion trap 140 in order to facilitate ion trapping, fragmentation and cooling. Ion trap 140 is additionally provided with at least one set of ion detectors 190 (wherein each set may consist of a single detector or multiple detectors) that generate a signal representative of the abundance of ions ejected from the ion trap.

Ion trap 140, as well as other components of mass spectrometer 100, communicate with and operate under the control of a data and control system (not depicted), which will typically include a combination of one or more general purpose computers and application-specific circuitry and processors. Generally described, the data and control system acquires and processes data and directs the functioning of the various components of mass spectrometer 100. The data and control system will have the capability of executing a set of instructions, typically encoded as software or firmware, for carrying out the analysis methods described herein.

Figure 2:
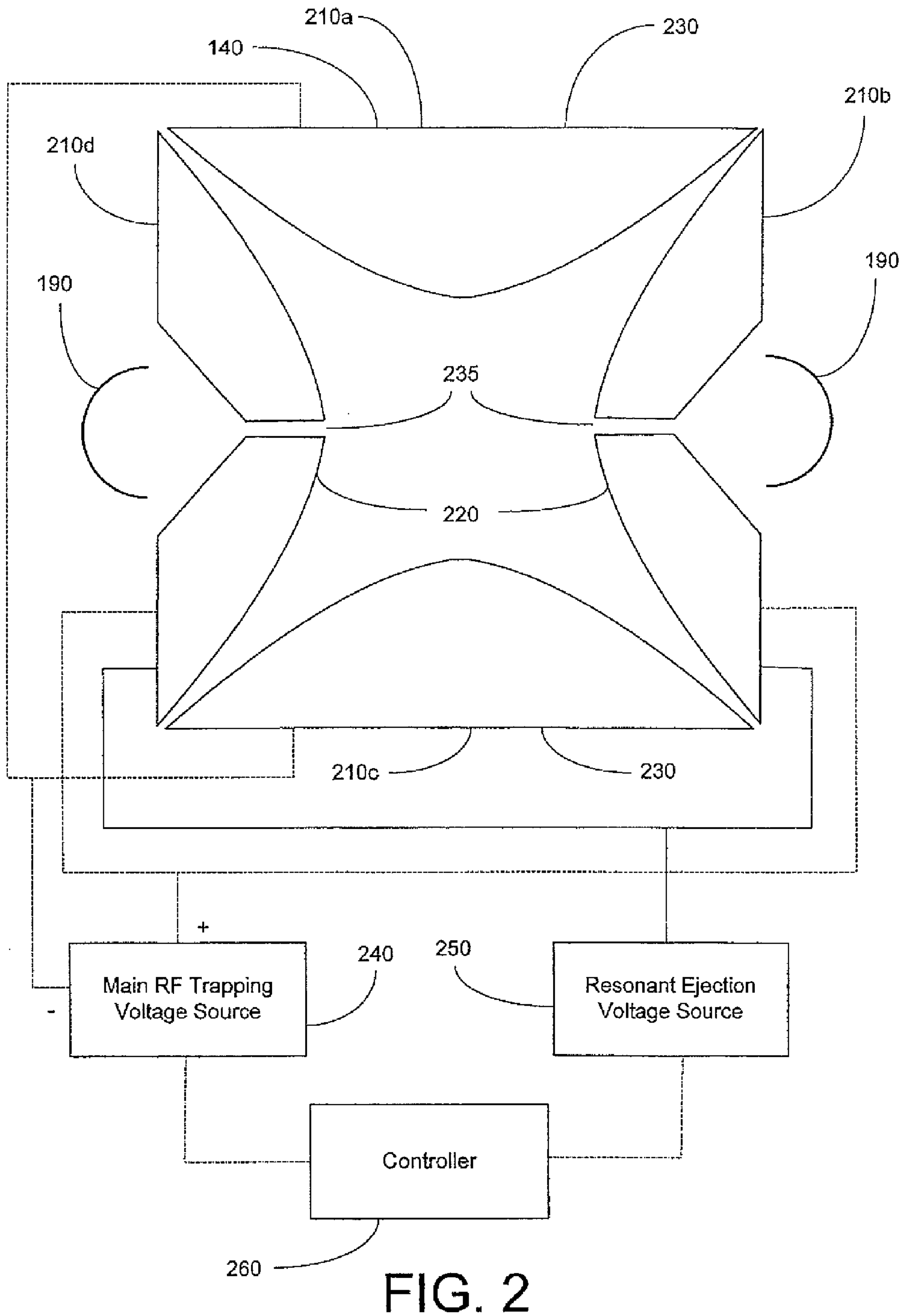
FIG. 2 is a lateral cross-sectional view of a two-dimensional radial ejection ion trap mass analyzer which may be used to implement methods and systems embodying the present invention.

FIG. 2 depicts a cross-sectional view of ion trap 140, which may be constructed as a conventional two-dimensional ion trap of the type described by Schwartz et al. in "A Two-Dimensional Quadrupole Ion Trap Mass Spectrometer", J. Am. Soc. Mass Spectrometry, 13: 659-669 (2002). Ion trap 140 includes four elongated electrodes 210*a*, 210*b*, 210*c*, 210*d*, each electrode having an inwardly directed hyperbolic-shaped surface, arranged in two electrode pairs 220 and 230 aligned with and opposed across the trap centerline. The electrodes of one electrode pair 220 are each adapted with an aperture (slot) 235 extending through the thickness of the electrode in order to permit ejected ions to travel through the aperture to an adjacently located detector 190. A main RF trapping voltage source 240 applies opposite phases of an RF voltage to electrode pairs 220 and 230 to establish a RF trapping field that radially confines ions within the interior of ion trap 140. During m/z analysis scans, resonant ejection voltage source 250 applies an oscillatory voltage across apertured electrode pair 220 to create a dipole excitation field. The amplitude of the applied main trapping RF voltage is ramped such that ions come into resonance with the excitation field in order of their m/z's. The resonantly or near resonantly excited ions develop unstable trajectories and are ejected through apertures 235 to detectors 190. Control of the main RF trapping voltage, resonant ejection voltage, and CID excitation voltage applied to electrodes of ion trap 140, specifically adjustment of their amplitudes, is effected by a controller 260 that forms part of the data and control system.

While FIG. 2 depicts a conventionally arranged and configured two-dimensional ion trap, practice of the invention should not be construed as being limited to any particular ion trap geometry or configuration. In an alternative implementation, the ion trap may take the form of a symmetrically stretched, four-slotted ion trap of the type described in the U.S. Pat. No. 8,415,617 by Jae C. Schwartz and entitled "Two-Dimensional Radial-Ejection Ion Trap Operable as a Quadrupole Mass Filter", the disclosure of which is herein incorporated by reference. The ion trap may also constitute a part of a dual ion trap mass analyzer structure disclosed in U.S. Pat. No. 7,692,142 for "Differential-Pressure Dual Ion Trap Mass Analyzer and Methods of Use Thereof" by Jae C. Schwartz et al, which is also incorporated herein by reference. The methods described herein may also be utilized in connection with conventional rotationally symmetric three-dimensional ion traps (including variants such as toroidal or cylindrical ion traps) as well as for rectilinear ion traps.

Figure 3:
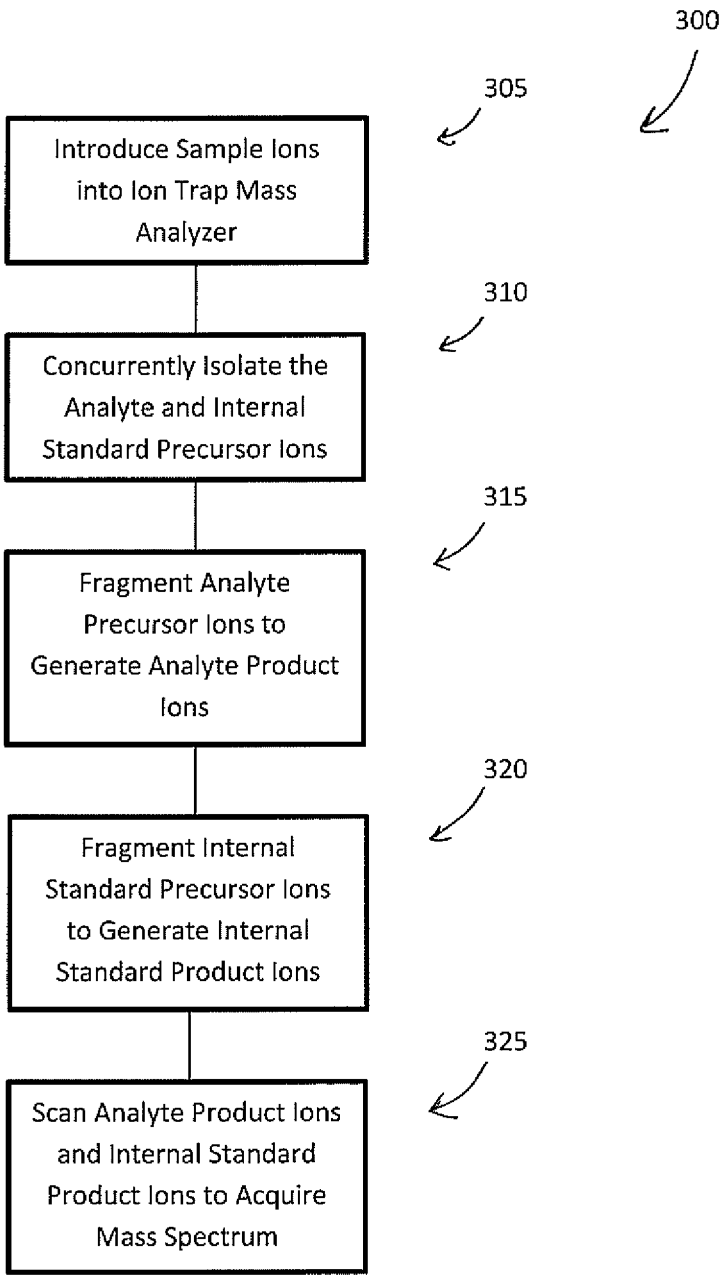
FIG. 3 is a flowchart depicting steps of a method of operating an ion trap mass analyzer for quantification of analytes in a sample, in accordance with one embodiment of the present invention.

FIG. 3 is a flowchart 300 depicting steps of a method of operating an ion trap mass analyzer for quantification of analytes in a sample, in accordance with one embodiment of the present invention. In certain implementations, the sample may take the form of a biological fluid, such as blood, plasma, saliva, or urine, or fraction thereof, or an extract from a biological tissue sample. The analyte may comprise, for example, a therapeutic drug or its metabolite, a drug of abuse or its metabolite, or an endogenous substance, such as creatinine or a steroid hormone. In step 305, sample ions, generated by the ionization source by ionizing molecules in the sample by an appropriate technique, are introduced into an ion trap mass analyzer. The sample ions include analyte precursor ions having a first mass-to-charge (m/z) ratio and internal standard precursor ions having a second m/z, different from the first m/z. As is known in the art, the internal standard from which the internal precursor ions are generated may consist of an isotopologue (e.g., a deuterated version) of the corresponding analyte. While the description set forth below discusses quantification of a single analyte, variants of this technique may quantify multiple analytes (e.g., a panel of two or more therapeutic drugs). The analyte precursor ions and the internal standard precursor ions are introduced into the ion trap mass analyzer from a common ion injection event, i.e. the analyte and internal standard precursor ions both enter the ion trap during a period defined by an injection start time (when the applied DC voltage(s) is/are set to allow the passage of ions into the ion trap) and an injection end time (when the applied DC voltage(s) is/are switched to a value that blocks the passage of ions into the ion trap).

Following the introduction of ions including the analyte and internal standard precursor ions into the ion trap, the analyte precursor ions and the internal standard precursor ions are isolated concurrently (step 310) by removing ions having m/z's other than those of the first and second precursor ions. As is known in the art, this operation is performed by applying oscillatory voltages to the ion trap electrodes to establish an electric field that kinetically excites the non-desired ions (those other than the analyte and internal standard precursor ions) such that the excited ions are ejected from the ion trap or are neutralized via collisions with electrode surfaces. In one illustrative implementation, concurrent isolation of the analyte and internal standard precursor ions is achieved by applying a notched multifrequency waveform voltage to the trap electrodes, as described in U.S. Pat. No. 9,048,074. In such waveforms, the frequency notches are set to correspond to the secular frequencies of the ions to be isolated, such that those ions are not sufficient kinetically excited to cause their ejection or dissociation.

According to a variant of the above-described technique, isolation of the analyte and the internal standard precursor ions may be performed concurrently with their introduction into the ion trap. This result may be achieved by applying an isolation waveform to the ion trap electrodes such that the non-selected ions—ions other than the analyte and internal standard precursor ions—are ejected from the ion trap or neutralized on its surfaces during the injection event.

Next, in step 315, the analyte precursor ions are fragmented to generate analyte product ions. In step 320, the internal standard precursor ions are fragmented to generate internal standard product ions. Further, the analyte precursor ions and the internal standard precursor ions can be fragmented simultaneously or successively. While FIG. 3 depicts the analyte precursor ions as being fragmented first and the internal standard precursor ions second, it should be understood that the present invention is not limited to this order of fragmentation. In some embodiments, the internal standard precursor ions can be fragmented first, with the analyte precursor ions being fragmented second, or both simultaneously.

Fragmentation in steps 315 and 320 may be carried out using well known ion trap type collision-induced dissociation (CID) by applying a first excitation waveform with a frequency which closely matches a secular frequency of the analyte precursor ions and a second excitation waveform with a frequency which closely matches a secular frequency of the internal standard precursor ions. In this manner, at least a portion of the analyte precursor ions and the internal standard ions undergo numerous collisions with atoms or molecules of collision gas (also referred to as background or damping gas) to cause them to become sufficiently vibrationally excited to fragment into analyte product ions and internal standard product ions.

Next, in step 325, an analytical scan is performed to mass-sequentially eject the analyte product ions and the internal standard product ions to the detector of the ion trap mass analyzer and thereby acquire a mass spectrum that includes both the analyte product ions and the internal standard product ions. As is known in the art and is discussed above, an analytical scan may be conducted in an ion trap mass analyzer by the resonant ejection method, in which a dipole excitation field is established within the ion trap, and a parameter of the RF trapping field is ramped (progressively varied) such that ions come into resonance with the excitation field in order of their m/z's, with the resonantly excited ions being ejected to a detector. The detector generates signals characteristic of the abundances of the ejected ions, which signals are processed by the data and control system to construct a product ion spectrum.

After acquisition of the product ion spectrum, the amount of the analyte present in the sample may be calculated by the data and control system using peak intensities in the spectrum. More specifically, provided that the internal standard is appropriately selected, at least one characteristic internal standard product ion species will uniquely correspond to the internal standard, such that its peak in the spectrum can be uniquely assigned to the internal standard, and at least one characteristic analyte product ion species will uniquely correspond to the analyte, such that its peak in the spectrum can be uniquely assigned to the analyte. As is depicted in the examples described below, the two peaks are sufficiently spaced apart in the spectrum (e.g., by at least 1 Thomson unit) so as to be clearly resolved in the spectrum. The data and control system may then determine the intensities of the peaks of the characteristic analyte product ion species and internal standard product ion species in the spectrum, and calculate the abundance of the analyte in accordance with a known (e.g., calibrated) relationship between analyte amount and the ratio of the intensities of these peaks, in a manner well known in the art.

Figures 4A, 4B, 4C:
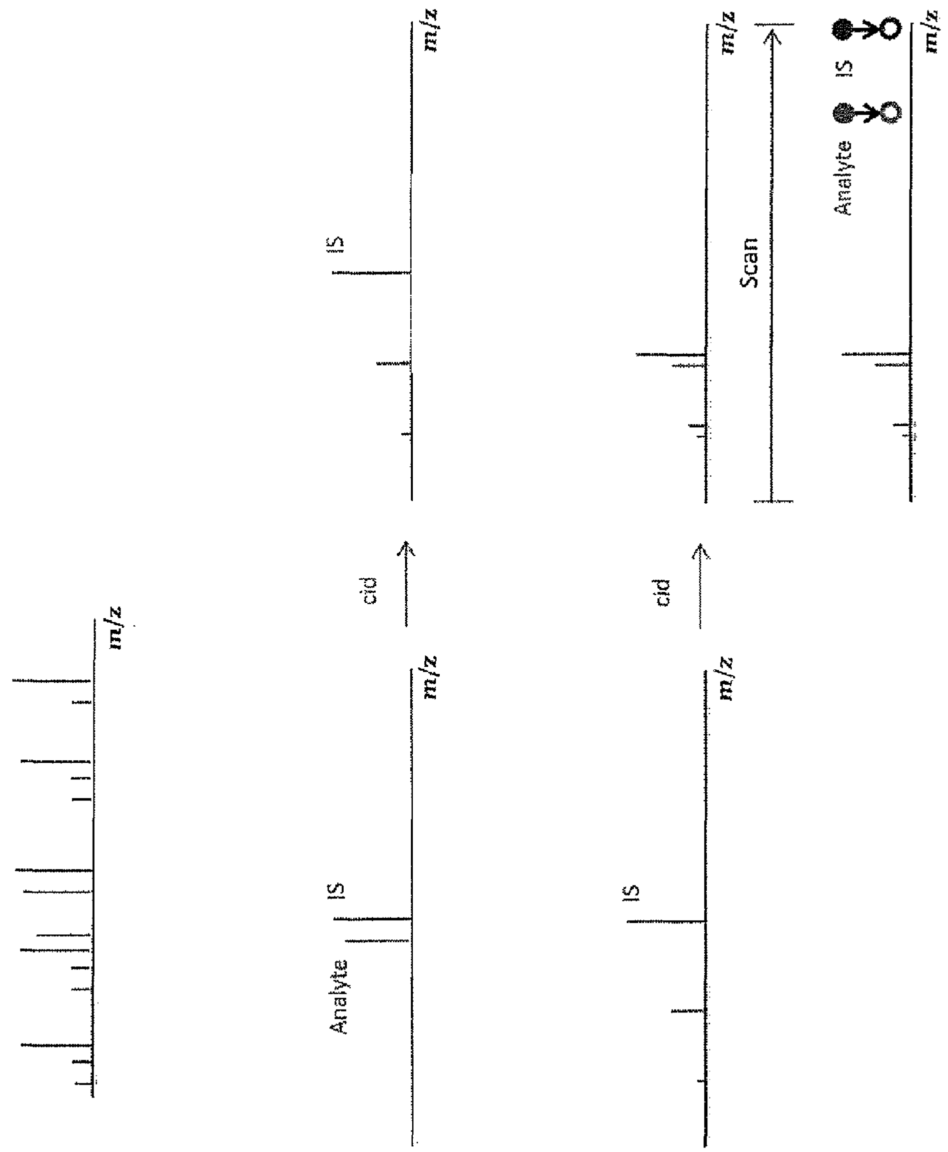
FIGS. 4A-4C show a series histograms or m/z spectra illustrating the evolution of the populations of ions confined within an ion trap mass analyzer or as well as those ejected in the m/z analysis scan from the ion trap mass analyzer during the performance of a method in accordance with the invention.

The results of the foregoing method steps are illustrated by the spectra depicted in FIGS. 4A-4C. FIG. 4A shows multiple species ion of different m/z ratios introduced into an ion trap mass analyzer from the same ion injection event. In this example, the precursor ions selected for MS2 quantitative analysis comprise analyte ions which are of lower m/z compared to corresponding internal standard ions.

FIG. 4B illustrates isolation and subsequent fragmentation of the analyte and internal standard precursor ions. First, ions other than those of the targeted analyte species and the corresponding internal standard are ejected in the process of ion isolation, as shown on the left side of FIG. 4B. As discussed above, a notched multifrequency waveform can be used to isolate the analyte species and its corresponding internal standard. After the analyte and internal standard ions are isolated, the analyte precursor ions are fragmented (for example, using the ion trap type CID technique with the excitation frequency tuned to match the secular frequency of the analyte ions), as shown on the right side of FIG. 4B. Subsequently, or simultaneously, to the dissociation of the analyte precursor ions, the internal standard precursor ions shown on the left side of FIG. 4C are dissociated (for example, using the CID technique with the excitation frequency tuned to match the secular frequency of the internal standard precursor ions), and the product ions of both the analyte and the internal standard are analyzed at the same time, as shown on the right side of FIG. 4C.

As a result, spectra of the product ions of the analyte and internal standard are obtained as a composite product ion spectrum. Abundance of product ions of different precursor ions of the analyte and the internal standard can be used to calculate the ratio of analyte versus internal standard.

EXPERIMENTAL SECTION

The following examples are set forth to further describe embodiments and aspects of the present invention but are not to be construed as limiting the scope thereof.

Figure 5A:
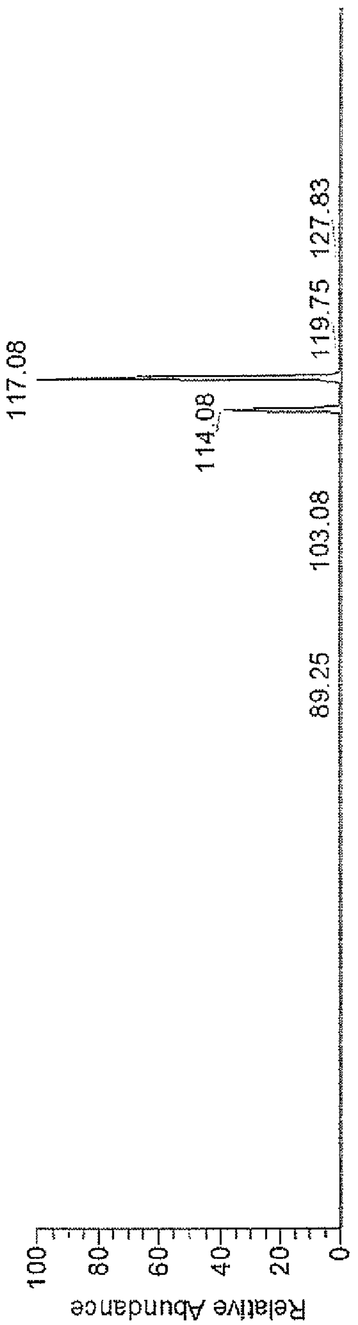
FIG. 5A shows precursor ions of creatinine and creatinine-d3 ionized using nano-electrospray ionization and isolated from any background ions.

FIG. 5A shows creatinine and creatinine-d3, ionized using nano-electrospray ionization and m/z isolated from any background ions with a dual-notch isolation waveform. In this example, a solution containing creatinine and creatinine-d3, each at a concentration of 100 ng/ml, was infused to an EASY-Spray™ probe at the speed of 0.5 μl/min. The spray voltage was approximately 4 kV.

Precursor ions of lower m/z, protonated creatinine, were firstly fragmented by trap type CID which is inherently m/z selective. After the fragmentation of the precursor ions of lower m/z, the precursor ions of higher m/z, protonated creatinine-d3, were fragmented.

Figure 5B:
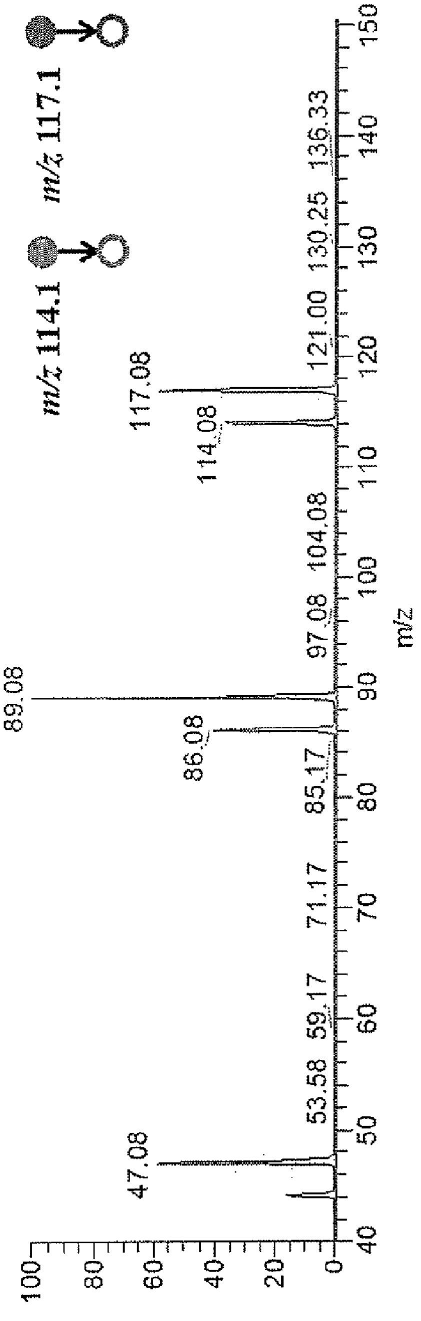
FIG. 5B shows the $MS^2$ m/z spectrum of the product ions of both creatinine and creatinine-d3, obtained using the embodiment of the present invention described in FIGS. 4A-4C.

After the fragmentation of the precursor ions of m/z 114.1 and 117.1 respectively, product ions of both creatinine and creatinine-d3 were analyzed at the same time and the $MS^2$ spectrum of the protonated creatinine and protonated creatinine-d3 was generated, as shown in FIG. 5B. The collision energy was set to be able to dissociate approximately 80% of the precursor ions. The remaining approximately 20% were still present in the spectra after fragmentations.

Figure 6A:
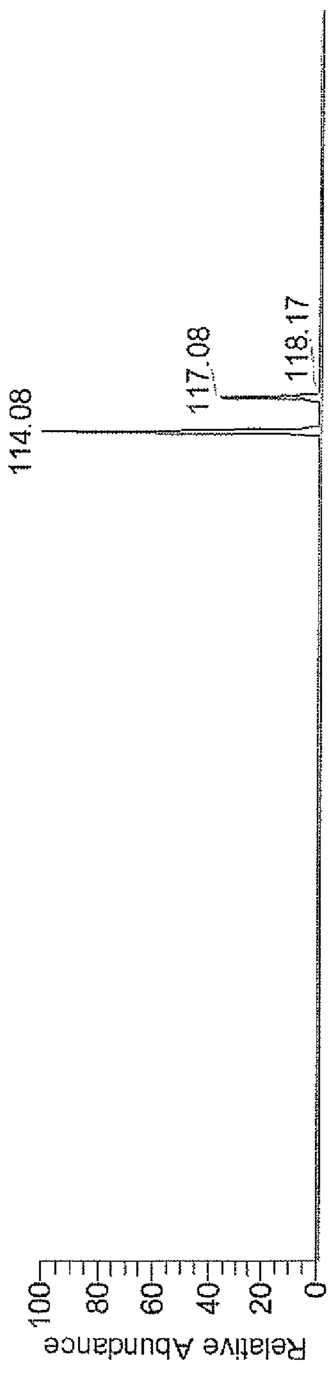
FIG. 6A shows isolated m/z peaks of protonated creatinine and creatinine-d3 using dried blood spots with paper spray ionization.

FIG. 6A shows isolated peaks of protonated creatinine and creatinine-d3 from dried blood spots using paper spray ionization. In this example, a 10 μl blood sample spiked with creatinine and creatinine-d3 at a concentration of (20+x) ug/ml and 10 ug/ml respectively, was deposited directly onto a disposable PaperSpray cartridge. After depositing the sample directly onto the disposable PaperSpray cartridge, the sample was absorbed into the paper substrate, allowed to dry and inserted into a PaperSpray auto-sampler for generating ions to the mass spectrometer. Pure methanol of 100 μl was applied to the paper to elute compounds from the matrix. A high voltage of approximately 4.5 kV was applied to the paper substrate via a contact on the cartridge to produce an electrospray from the paper tip.

Figure 6B:
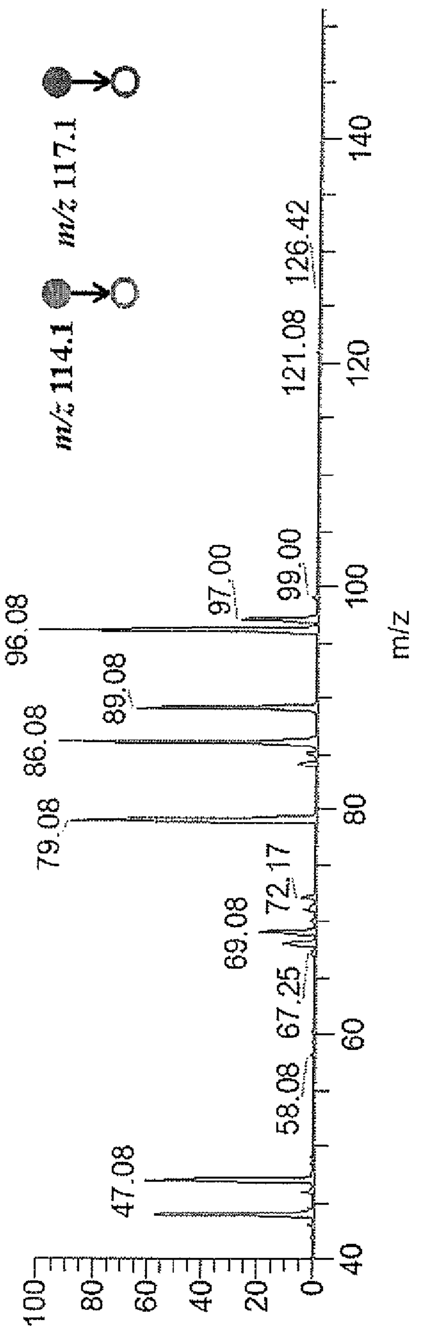
FIG. 6B shows the $MS^2$ m/z spectrum of product ions of protonated creatinine and protonated creatinine-d3 after fragmentation of the precursor ions of m/z 114.1 and 117.1.

FIG. 6B shows the $MS^2$ spectrum of the protonated creatinine and protonated creatinine-d3 after fragmentation of the precursor ions of m/z 114.1 and 117.1. Product ions of m/z 43.1, 86.1, 47.1, 89.1 from the protonated creatinine and protonated creatinine-d3 were observed to be distinct.

Figure 7:
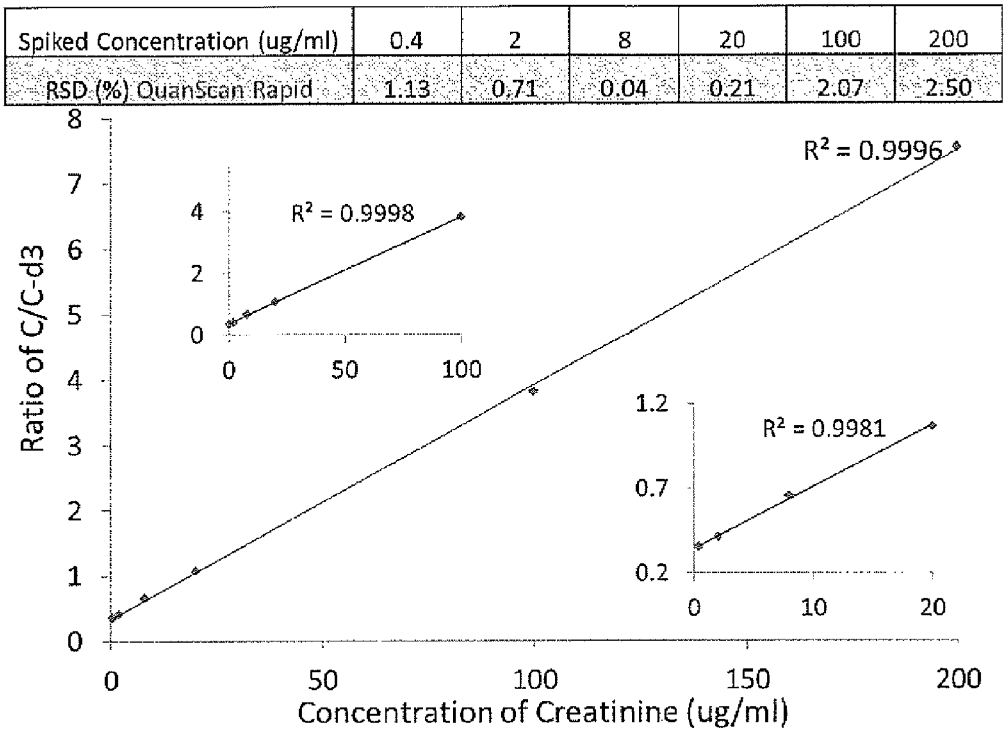
FIG. 7 is a quantitative calibration curve showing the ratio of creatinine/creatinine-d3 in blood with paper spray ionization over the concentration range from 0.4 μg/ml to 200 μg/ml using the embodiment of the present invention described in FIGS. 4A-4C.

A set of experiments were conducted to explore the improvement of RSD the embodiments of the present invention could make. A series of dried blood samples containing the internal standard creatinine-d3 at 10 μg/ml and the analyte creatinine at different spiked concentrations from 0.4 to 200 μg/ml were analyzed to develop a calibration curve for quantitation as shown in FIG. 7. Ion abundance of product ions of 43.1 and 86.1 were summed to represent the abundance of creatinine. Ion abundance of product ions of 47.1 and 89.1 were added up to represent the abundance of creatinine-d3. 10 μl blood was applied to the PaperSpray cartridge and air-dried for up to two hours. Pure methanol of 100 μl, 30 ul, and 20 ul were then applied to the paper to elute compounds from the matrix at t=0 min, 5 min, and 8 min, respectively. The dried blood sample on each PaperSpray cartridge was analyzed for approximately 10 minutes with multi applications of organic solvent. The spray voltage was approximately 4.5 kV. Error bars were plotted but may not be seen until zoomed in.

For each point in the curve, the samples were analyzed and the creatinine/creatinine-d3 ratio was calculated by dividing the ion abundance of 43.1 and 86.1 by the ion abundance of 47.1 and 89.1. The calibration curve was linear over the range from 0.4 μg/ml to 200 ug/ml. More significantly, RSD values across the whole range were less than 3%. The RSD values of concentrations of 2, 8, and 20 μg/ml were less than 1%.

The advantages of the present invention include higher efficiency of sample utilization. Multiple precursor ions of different m/z can be analyzed with a single ion injection event, allowing time for more analytical scans to be performed. Other features and advantages include a simple hardware configuration to practice embodiments of the present invention. For example, a single linear ion trap mass spectrometer configuration allows the analysis to be performed at a simple, low cost, and robust system. Thus, the present invention eliminates any requirement of a complicated configuration in hardware to analyze precursor ion species with different m/z using the same ion injection event.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made in the embodiments chosen for illustration without departing from the spirit and scope of the invention.

What is claimed is:

1. A method of operating an ion trap mass analyzer for quantification of analytes in a sample, comprising:

a. introducing sample ions into the ion trap mass analyzer in a single injection event, the sample ions including analyte precursor ions having a first mass-to-charge ratio (m/z) and internal standard precursor ions having a second m/z;

b. concurrently isolating the analyte precursor ions and the internal standard precursor ions;

c. fragmenting the analyte precursor ions to generate analyte product ions;

d. fragmenting the internal standard precursor ions to generate internal standard product ions, wherein at least one characteristic product ion species of the analyte product ions uniquely corresponds to the analyte, and at least one characteristic product ion species of the internal standard product ions uniquely corresponds to the internal standard; and e. mass-sequentially ejecting the ions to a detector to acquire a mass spectrum containing the analyte product ions and the internal standard product ions.

2. The method of claim 1 further comprising determining an amount of the analyte in the sample using a relationship between intensities of the at least one characteristic analyte product ion species and the at least one characteristic internal standard product ion species in the mass spectrum.

3. The method of claim 1 further comprising applying a notched waveform to concurrently isolate the analyte precursor ions and the internal standard precursor ions from any background ions.

4. The method of claim 1 wherein the fragmenting is carried out using collision-induced dissociation (CID).

5. The method of claim 1 wherein the analyte is a therapeutic drug or its metabolite.

6. The method of claim 1 wherein the analyte is a drug of abuse or its metabolite.

7. The method of claim 1 wherein the analyte is an endogenous substance in a biological medium.

8. The method of claim 1 wherein the internal standard is an isotopologue of the analyte.

9. The method of claim 1 wherein the step of introducing sample ions into the ion trap mass analyzer includes generating ions from a sample using a direct sampling ion source.

10. The method of claim 9 wherein the sample is a biological fluid.

11. An ion trap mass spectrometer system, comprising:

a. an ion source configured to generate sample ions including analyte precursor ions having a first mass-to-charge ratio (m/z) and internal standard precursor ions having a second m/z;

b. an ion trap mass analyzer positioned and adapted to receive the sample ions in a single injection event, the ion trap mass analyzer having a controller programmed to apply voltages to the ion trap mass analyzer to cause the ion trap mass analyzer to perform the steps of: concurrently isolating the analyte precursor ions and the internal standard precursor ions; fragmenting the analyte precursor ions to generate analyte product ions and the internal standard precursor ions to generate internal standard product ions, wherein at least one characteristic product ion species of the analyte product ions uniquely corresponds to the analyte, and at least one characteristic product ion species of the internal standard product ions uniquely corresponds to the internal standard; and mass-sequentially ejecting the ions to a detector to acquire a mass spectrum containing the analyte product ions and the internal standard product ions; and c. a data and control system programmed to determine an amount of the analyte in the sample using a relationship between intensities of the at least one characteristic analyte product ion species and at least one characteristic internal standard product ion species in the mass spectrum.

12. The system of claim 11 wherein the controller is programmed to apply a notched waveform to the ion trap mass analyzer to isolate the analyte precursor ions and the internal standard precursor ions from any background ions.

13. The system of claim 11 wherein the controller is programmed to apply excitation voltages to the ion trap mass analyzer to fragment the analyte precursor ions and the internal standard precursor ions by collision-induced dissociation (CID).

14. The system of claim 11 wherein the ion source comprises a direct sampling ion source.

15. The system of claim 11 wherein the analyte is a therapeutic drug or its metabolite.

16. The system of claim 11 wherein the analyte is a drug of abuse or its metabolite.

17. The system of claim 11 wherein the analyte is an endogenous substance in a biological medium.

18. The system of claim 11 wherein the internal standard is an isotopologue of the analyte.

19. The method of claim 1 wherein the analytes in the sample are quantified using a single ion trap mass analyzer.

20. The system of claim 11 wherein the ion trap mass analyzer is a single ion trap mass analyzer.

* * * * *